(12) United States Patent
Moser et al.

(10) Patent No.: US 7,976,509 B2
(45) Date of Patent: Jul. 12, 2011

(54) INJECTION DEVICE WITH SECURED DOSING BUTTON

(75) Inventors: Ulrich Moser, Heimiswil (CH); Christian Schrul, Burgdorf (CH); Jürg Hirschel, Aarau (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 12/171,793

(22) Filed: Jul. 11, 2008

(65) Prior Publication Data

US 2009/0054846 A1 Feb. 26, 2009

Related U.S. Application Data (63) Continuation of application No. PCT/CH2007/000018, filed on Jan. 15, 2007.

(30) Foreign Application Priority Data

Jan. 17, 2006 (DE) .......................... 10 2006 002 383
Feb. 1, 2006 (DE) .......................... 10 2006 004 561

(51) Int. Cl.
*A61M 5/00* (2006.01)
*A61M 37/00* (2006.01)

(52) U.S. Cl. ..................... 604/211; 604/191; 604/90

(58) Field of Classification Search .............. 604/90, 604/207, 211, 191, 181; 222/136, 14
See application file for complete search history.

(56) References Cited

U.S. PATENT DOCUMENTS

| | | | |
|---|---|---|---|
| 4,820,287 A | 4/1989 | Leonard | |
| 4,968,299 A * | 11/1990 | Ahlstrand et al. | 604/90 |
| 5,279,586 A * | 1/1994 | Balkwill | 604/207 |
| 5,480,387 A | 1/1996 | Gabriel et al. | |
| 5,536,249 A * | 7/1996 | Castellano et al. | 604/65 |
| 5,679,111 A | 10/1997 | Hjertman et al. | |
| 5,807,346 A | 9/1998 | Frezza | |
| 6,193,698 B1 | 2/2001 | Kirchhofer et al. | |
| 6,235,004 B1 * | 5/2001 | Steenfeldt-Jensen et al. | 604/207 |
| 6,663,602 B2 | 12/2003 | Moller | |
| 6,793,646 B1 * | 9/2004 | Giambattista et al. | 604/90 |
| 7,169,133 B2 | 1/2007 | Broennimann et al. | |
| 2001/0009990 A1 | 7/2001 | Hostettler | |
| 2002/0173752 A1 | 11/2002 | Polzin | |
| 2004/0019333 A1 | 1/2004 | Graf et al. | |
| 2004/0108339 A1 * | 6/2004 | Hansen et al. | 222/326 |

(Continued)

FOREIGN PATENT DOCUMENTS

DE 603401 10/1934

(Continued)

*Primary Examiner* — Theodore J Stigell
*Assistant Examiner* — Bradley G Thomas, Jr.
(74) *Attorney, Agent, or Firm* — Dorsey & Whitney LLP (57) ABSTRACT

An injection device including an accommodating device for a substance to be delivered, e.g. a vial or ampoule holder, which is insertable into and can be displaced relative to the injection device or a part thereof; an adjusting element for adjusting a dose to be administered from the injection device, which element is inserted in the injection device; and a coupling element for coupling the accommodating device to the adjusting element so that the adjusting element is at least partially moved out from the injection device when the accommodating device is inserted. A method for preparing an injection device using a dual chamber vial or ampoule to administer a substance, wherein the method involves using an adjusting device which is released, extended or pushed out from the injection device not before or after the substance to be administered from dual chamber vial or ampoule is mixed.

24 Claims, 7 Drawing Sheets

U.S. PATENT DOCUMENTS

| | | | |
|---|---|---|---|
| 2004/0186441 A1* | 9/2004 | Graf et al. | 604/207 |
| 2004/0186442 A1* | 9/2004 | Graf et al. | 604/207 |
| 2005/0090782 A1* | 4/2005 | Marshall et al. | 604/211 |
| 2005/0137571 A1 | 6/2005 | Hommann | |
| 2005/0209570 A1* | 9/2005 | Moller | 604/207 |
| 2005/0222540 A1* | 10/2005 | Kirchhofer et al. | 604/207 |
| 2008/0009807 A1 | 1/2008 | Hommann | |

FOREIGN PATENT DOCUMENTS

| | | |
|---|---|---|
| DE | 1053143 | 3/1959 |
| DE | 3030239 C2 | 2/1982 |
| DE | 197 30 999 C1 | 12/1998 |
| DE | 101 60 393 | 6/2003 |
| DE | 101 60 393 A1 | 6/2003 |
| DE | 10 2004 004 310 | 8/2005 |
| DE | 10 2004 004 310 A1 | 8/2005 |
| EP | 0 373 321 A1 | 6/1990 |
| EP | 897 729 | 2/1999 |
| EP | 897 729 A2 | 2/1999 |
| EP | 0 713 403 B1 | 12/1999 |
| WO | WO 00/62839 A | 10/2000 |

* cited by examiner

INJECTION DEVICE WITH SECURED DOSING BUTTON

CROSS-REFERENCED RELATED APPLICATIONS

This application is a continuation of International Patent Application No. PCT/CH2007/000018 filed Jan. 15, 2007, which claims priority to German Patent Application No. DE 10 2006 002 383.8 filed Jan. 17, 2006 and German Patent Application No. DE 10 2006 004 561.0 filed Feb. 1, 2006, the entire content of all of which is incorporated herein by reference.

BACKGROUND

The present invention relates to devices for administering, injecting, infusing, delivering or dispensing a substance or product, and to methods of making and using such devices. More particularly, it relates to a device for administering a substance, e.g. an injection device or an injection pen, which has a dose setting element for setting or selecting and administering a set or selected dose of an injectable product. In some preferred embodiments, the injection device is used for self-administering the product, takes the form of a disposable injector and may be used with, for example, a single-chamber or two-chamber ampoule.

Injection pens are widely used due to their size and shape, which makes them easy to handle when self-administering medicaments. Particularly if self-administering a medicament, such as insulin or a hormone for example, ease of handling, accuracy of the set dose and safety when setting a dose are of major importance.

Patent specification DE 10 2004 004 310, filed by the owner of the present application, discloses an injection device with a dose setting element, which effects a forward driving movement relative to the housing of the injection device in a forward drive direction and a dose setting movement in the direction opposite the forward driving movement and is coupled with a conveying mechanism so that the forward driving movement causes a conveying movement of the conveying mechanism, and the length of a distance defining the dose to be dispensed which is travelled by the dose setting element during the forward driving movement is set by the dose setting movement. A first catch mechanism is formed by the housing in a sleeve portion surrounding the dose setting element and a second catch mechanism is formed by the dose setting element or a separate, additional dose setting catch body, and a catch engagement of the catch mechanisms can be released by a dose setting movement of the dose setting element or the separate, additional dose setting catch body without involving a rotating movement.

U.S. Pat. No. 5,807,346 discloses a measuring instrument for dispensing different doses of a liquid, which has a reservoir for accommodating the liquid, a displaceable toothed rack element axially disposed inside and a pushing element which can be operated by the user. Annular notches are provided on the toothed rack element and the housing has various axial slots distributed across its periphery. An outwardly projecting pin is provided on the pushing element, which is able to locate in one of the axial slots of the housing, and the setting element can be easily extracted by the user.

Patent specification EP 0 713 403 B1 discloses a syringe with a barrel, which defines or has a cylinder, and the cylinder has a nozzle at one end and encloses a plunger which is able to slide in the longitudinal direction inside the cylinder, and the distance by which the plunger is able to move inside the cylinder defines the volume administered by the syringe, and the plunger is drivingly coupled with a slide which is disposed so that it moves parallel with the plunger, and the distance in length by which the plunger is able to slide inside the cylinder is defined by the movement restrictions of a stop surface on the barrel or the slide by reference to end stops on the slide or barrel. The syringe can be locked in a state in which the stop surface and the end stops are able to move only within movement limits with respect to one another, which can be selected from two or more pre-selectable predefined movement limits, and the stop surface has an insert which can be inserted from an orifice in the barrel or slide so that it projects out from it and is difficult to remove from them or can be so only by using a special tool, and the projecting part of the insert acts as a stop surface, and the position of each such orifice relative to the end stops defines one of the predefined movement distances.

SUMMARY

One object of the present invention is to provide an injection device which improves ease of setting or selecting a dose while simultaneously reducing the likelihood of incorrect operation.

In one embodiment, the present invention comprises an injection device comprising an accommodating device for a substance to be delivered, e.g. a vial or ampoule holder, which is insertable into and can be displaced relative to the injection device or a part thereof, an adjusting element for adjusting or selecting a dose to be administered from the injection device, which element is in, partially in or inserted in the injection device, and a coupling element for coupling the accommodating device to the adjusting element so that the adjusting element is moved relative to, e.g., at least partially moved out from, the injection device when the accommodating device is inserted. The present invention further comprises a method for preparing an injection device using a dual chamber vial or ampoule to administer a substance, wherein the method involves using an adjusting device which is moved, released, extended or pushed out from the injection device not before or after the substance to be administered from dual chamber vial or ampoule is mixed.

In one embodiment, the present invention comprises an injection device comprising a device accommodating a substance to be delivered, e.g. a vial or ampoule holder, which can be displaced relative to the injection device or a part thereof; an adjusting element for adjusting a dose to be administered from the injection device, which element is inserted in the injection device; and a coupling element for coupling the accommodating device to the adjusting element so that the adjusting element is at least partially pushed out of or extended from the injection device when the accommodating device is inserted. A method for preparing an injection device for administration of a substance is encompassed, wherein the method comprises using an adjusting device which is released or extended or pushed out from the injection device not before or after a dual chamber vial is mixed.

By virtue of one aspect of the present invention, an injection device in accordance with the present invention comprises a holder device for a substance to be administered, into which the substance to be administered can be introduced directly or in a container, for example an ampoule, in which case the holder device is designed to receive, accommodate and/or hold an ampoule. The holder device can be moved relative to the injection device and an element of the injection device constituting the holder or ampoule holder can be pushed into or screwed into it or a part of it, for example into the housing of the injection device, so that if using a known two-chamber ampoule, the substances contained in the two-chamber ampoule are mixed during the pushing-in or screwing-in operation and can thus be prepared for administering to a patient.

A dose setting or setting element is also provided, for example a rotating knob, for setting or selecting the dose of substance to be administered from the injection device. The quantity or dose of the substance to be administered can be selected or fixed on the basis of a rotary position of the setting or dose setting element. In some preferred embodiments, in an initial state, the dose setting element is pushed so far into the injection device that it cannot be gripped by a user or can only be gripped with great difficulty and not be easily pulled out.

In accordance with the present invention, the holder device for the substance to be dispensed which can be introduced into or pushed into the injection device, for example a screw-in or push-in ampoule holder, is coupled with the setting element so that as the holder device is being pushed into or having been completely or almost completely pushed into the injection device or into a housing, the setting element is at least partially pushed out of the injection device or a housing thereof so that it can be operated by a user to set a dose. The dose setting or setting element may be provided in the form of a rotatable dose setting knob of a type known per se, which is disposed at the proximal (rear) end of the injection device and fixedly connected to a dose setting knob sleeve which can be pushed axially into the injection device and moved out of it to move out the dose setting knob, thereby releasing it in readiness for setting a dose.

In some preferred embodiments, the dose setting element may be coupled with the injection device so that it cannot be rotated when the injection device is in the pushed-in state and can only be rotated to set a dose after being pushed out. Specific details of the design of the dose setting system may be found in the explanations given herein below. The dose setting element may be designed so that after setting the dose to be administered in a pre-set defined position extracted from the injection device in which it can be rotated to set the dose, it can be extracted farther out of the injection device to load the injection device, in which case the dose setting element may be locked to prevent rotation during the extra extraction operation or alternatively also rotatable. Another option is one wherein the dose is not set until after the dose setting element has been loaded or extracted from the injection device and the dose setting element is not locked to prevent rotation until it is pushed back into the injection device to administer the substance.

In an initial or the pushed-in state, for example, the setting element may be retained in the injection device or a housing of the injection device by static friction or a catch mechanism. The force of the static friction or the catch mechanism can be overcome by pushing in the substance holder device to extend the setting element from the injection device. For example, a proximal face of the substance holder element or a combined setting element-extraction element disposed on it may move into contact with the setting element or dose setting element or may be connected to or coupled with the dose setting element by one or more other elements locked relative to the injection device, such as a guide sleeve. This can be accomplished, for example, by a releasable catch mechanism or holder, so that a pushing-in or screwing-in movement of the substance holder device causes the setting or dose setting element to be pushed out. A catch element or other blocking or lock element may also be provided, which holds the dose setting element in the injection device in the pushed-in state and can be released from the substance holder element directly or from an element coupled with it to enable the dose setting element to be pushed out.

In some preferred embodiments, a plunger rod, toothed rack or the like is provided in the injection device so that a proximal stopper or displacement body provided in the substance holder device or in an ampoule is pushed into the injection device relative to the substance holder region during the operation of pushing in or screwing in the substance holder device. In other words the stopper is pushed into the ampoule as a result of which, in the case of a two-chamber ampoule, mixing of the components contained in the chambers of the two-chamber ampoule is initiated and then terminated when the plunger rod or toothed rack has been pushed sufficiently far in. Thus, the two-chamber ampoule is mixed in readiness for preparing to administer the substance.

In some preferred embodiments, the coupling between the substance holder element and dose setting element is designed so that the dose setting element is not moved or pushed out of the injection device until the substance holder element has been completely or almost completely inserted or introduced, for fully or almost fully mixing the substances contained in the two-chamber ampoule. For example, it may be that the dose setting element is not coupled with the substance holder element until the last part of the insertion path, for example the last 6 mm, and the dose setting element is not pushed out of the injection device until after coupling, e.g. once the proximal (rear) end of the substance holder element has made contact with the dose setting element having travelled the remaining exemplary insertion distance of 6 mm, so that the dose setting element can be gripped by a user and rotated to set the dose or pulled out farther to prime the pen.

It is of advantage to provide a marking on the dose setting element, for example on the circumferential face of the dose setting knob or a dose setting knob sleeve, which may be marked to assist with setting a dose and/or indicate dose units. The dose display may be printed on or applied to the dose setting element so that it is not visible until the dose setting element has been pushed out, in which case the dose setting element is pushed out sufficiently so that the dose display can be seen by a user, or the display printed on the dose setting element is pushed into the region of a viewing widow disposed in the housing of the injection device thereby rendering it visible.

In accordance with the present invention, in a method for preparing an injection device for administering a dose of substance, a dose setting element pushed or moved into the injection device which can not be gripped by a user or can be gripped only with great difficulty is not pushed or moved out of the injection device until during or after pushing a substance holder element, e.g. an ampoule holder or an ampoule, into the injection device so that the setting or dose setting element can not be gripped and operated by a user until then.

By virtue of another aspect, the present invention relates to an injection device with a housing and a substance dispensing element which can be moved relative to the housing, to force a substance contained in the injection device out of the injection device for dispensing by moving the dispensing element, e.g. pushing the dispensing element into the injection device. At least one blocking element is provided in the injection device, which, when a substance has been dispensed from the injection device once by the dispensing element, prevents another dose from being administered. The dispensing element may be coupled with a dose setting element or, in some embodiments, the functions may be combined in one element. A dose is set by a rotation of the dispensing element, the injection device is primed by pulling out the dispensing element and the substance is actually dispensed by pushing the dispensing element in. In some preferred embodiments, the dispensing element may be a rotating or dose setting knob of the injection device. In some embodiments, the dispensing element may be a housing part of the injection device which is able to move relative to another element or housing part of the injection device.

In some preferred embodiments, a blocking, lock or catch element is provided on the dispensing element, for example a catch cam and/or a groove, which, during or after a the dispensing operation, is able to establish a connection with a co-operating complementary element, in other words a co-operating groove or catch cam of the injection device or of an ampoule. In some preferred embodiments, the connection can not be released or can be released only with great difficulty once a set dose has been dispensed from the injection device. The blocking or catch element may co-operate with a plunger rod or toothed rack of the injection device, for example, and the complementary element may be a catch element disposed on a flexible arm, for example, such as a catch cam, extending into the dispensing element. Thus, a positive connection can be established between the dispensing element and the toothed rack or plunger rod once the substance has been dispensed. The dispensing element can then no longer be moved relative to the toothed rack or plunger rod. The dispensing element may also be blocked or locked relative to the injection device or a housing thereof, for example by a catch connection, during or after a dispensing operation, to prevent another dispensing operation. Another option is to lock or block only a movement of the dispensing element in a specific direction, for example an axial movement and/or a rotating movement, to prevent any possibility of more substance being dispensed from the injection device due to the locked or prevented direction(s) of movement.

With respect to the method in accordance with the present invention, i.e., a method for dispensing a substance from an injection device and/or for locking the injection device, a dispensing element triggering or causing dispensing of the substance may be blocked or locked before, during or after dispensing a set dose of the substance to be administered so that the dispensing element can no longer be moved in the direction which would trigger further or another dispensing of the substance from the injection device. This being the case, a quantity or dose of the substance to be dispensed set or pre-set once by a user can be dispensed from the injection device only once, and any further dispensing of the substance can be prevented, even if there is a quantity of substance left in the injection device. This is necessary, in some cases, if mixing substances in two-chamber ampoules, wherein the substances or the mix can deteriorate or change in quality after a certain time to the extent that it would not be advisable and could possibly be damaging to the health if the mix were administered to a patient again or after the certain period of time.

DETAILED DESCRIPTION

Figure 1A:
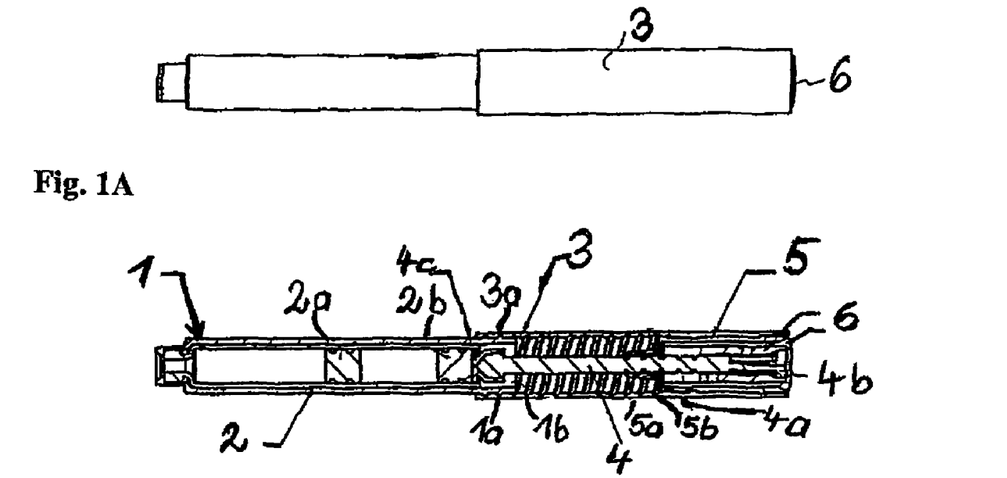
FIGS. 1A to 1E show the sequence or operation or steps involved in setting dose of a substance and dispensing the dose based on an embodiment of an injection device in accordance with the present invention, seen respectively in plan view and in cross-section.

FIG. 1A is a plan view and cross-section illustrating one embodiment of an injection device in accordance with the present invention, with an ampoule holder 1 serving as a substance holder, in which a two-chamber ampoule 2 incorporating two displaceable stoppers 2a and 2b can be fitted. The ampoule holder 1 is displaceable relative to the housing of the injection device which, in the embodiment illustrated, is provided in the form of threaded sleeve 3, and can be screwed into the internal thread 3a of the threaded sleeve 3 due to an engagement with the external thread 1a provided on the proximal end of the ampoule holder 1. A guide sleeve 5 is connected to the threaded sleeve 3 by an annular web 3c provided on the internal face of the threaded sleeve 3 locating in the circumferentially extending groove 5d (see FIG. 2A) on the external face of the guide sleeve 5 and has catch elements 5a biased radially inwardly at its distal end which locate or are receivable in co-operating grooves or teeth 4a of a toothed rack 4 which is prevented from rotating by axially extending grooves, thereby securing it so that it cannot move in the proximal (rearward) direction. However, the toothed rack 4 can be moved in the distal (forward or injection) direction relative to the guide sleeve 5, and the catch elements 5a provided on elastic arms slide out of the grooves or teeth 4a of the toothed rack and snap into a subsequent groove or tooth 4a. In the embodiment illustrated, a dose setting knob serving as a dispensing and dose setting element 6 is provided at the proximal end, which is pushed so far into the housing or into the threaded sleeve 3 that it can not be practically or easily gripped by a user. When the injection device is in the position illustrated in FIG. 1A, which may also be termed the delivery position, only the ampoule holder 1 can be moved, in other words screwed into the threaded sleeve 3, to mix the substances contained in the two-chamber ampoule 2. However, it is not yet possible to effect a setting operation by using the dose setting knob 6.

Figure 1B:
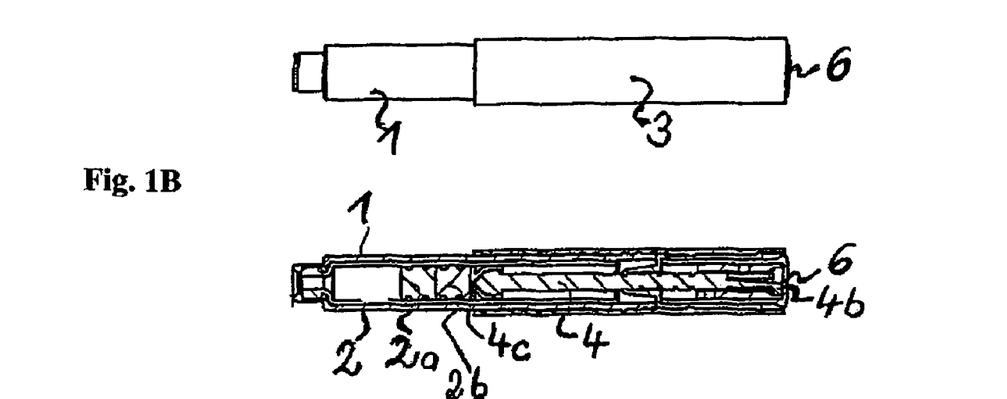

FIG. 1B shows the injection device illustrated in FIG. 1A but in the mixing position after the ampoule holder 1 has been screwed into the threaded sleeve 3. By pushing the ampoule 2 retained by the ampoule holder 1 in the proximal direction, the shoulder 4c seated on the front face of the toothed rack 4 is moved into the ampoule 2, as a result of which the adjacently lying stopper 2b is pushed into the ampoule 2 to initiate mixing in the ampoule 2 in a known manner. Priming may also take place at the same time.

Figure 1C:
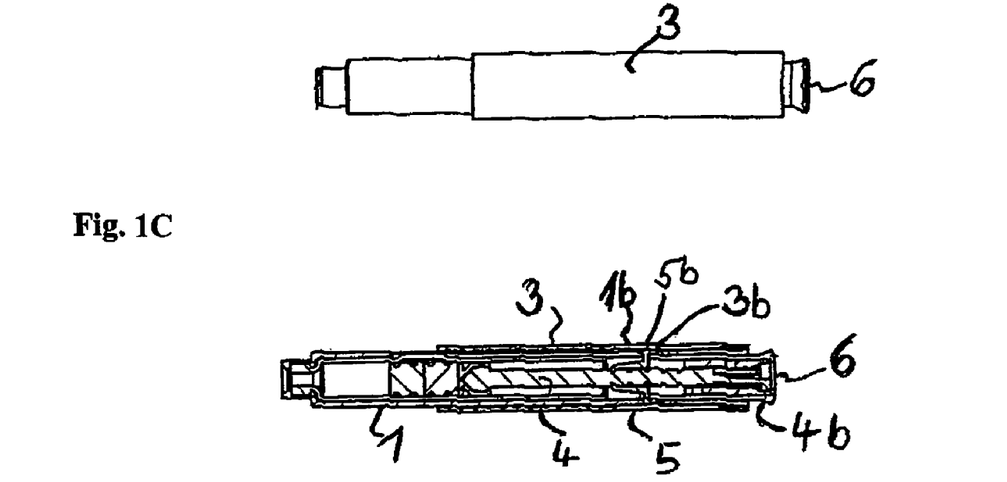

As illustrated in FIG. 1C, the ampoule holder 1 may be screwed into the threaded sleeve 3 of the injection device until a proximal (rear) contact surface 1b of the ampoule holder 1 sits against the radially outer distal or front face of the guide sleeve 5. If the ampoule holder 1 is screwed farther in, the guide sleeve 5 moves in the proximal direction relative to the threaded sleeve 3 together with the ampoule holder 1 so that the catch connection (formed by elements 3c, 5d) is released until a stop element 5b provided on the external face of the guide sleeve 5 has moved against a complementary stop element 3b on the internal face of the threaded sleeve 3, thereby restricting the turning movement of the ampoule holder 1. Due to the movement of the guide sleeve 5 in the proximal direction, the dose setting knob 6 mounted in the guide sleeve 5 is pushed in the proximal direction out of the injection device so that the dose setting knob 6 can be used to set a dose to be dispensed from the injection device. As this happens, the annular web 3c moves into engagement with the circumferentially extending grooves 5e (priming position) and 5f (end position) of the guide sleeve 5 which is pushed past by the ampoule holder 1 lying against the guide sleeve 5.

Figure 1D:
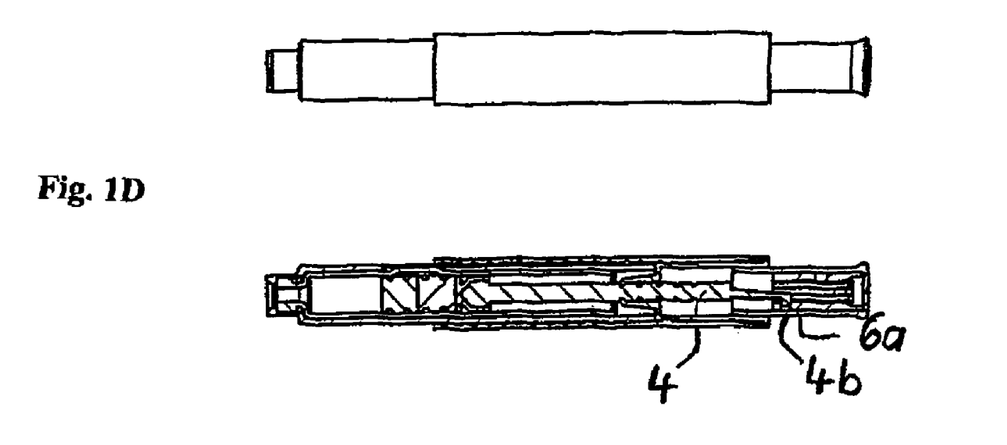
Figure 1E:
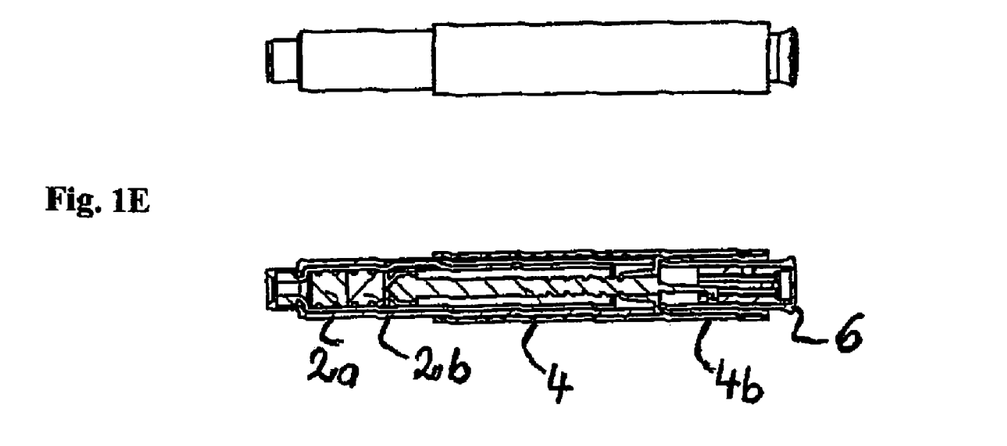

FIG. 1D shows the primed injection device with the dose setting knob 6 pulled out of the injection device until a catch element 4b disposed on the toothed rack 4 and projecting in the proximal direction latches in a catch orifice 6a provided on the internal face of the dose setting knob 6. The toothed rack 4 latched in this manner can be pushed in the distal direction of the injection device due to a pressure applied to the dose setting knob 6, as illustrated in FIG. 1E, to push the stoppers 2a and 2b disposed in the ampoule 2 in the distal direction and dispense the already mixed medicament from the ampoule 2. When the dose setting knob 6 is pushed back into the pen or into the threaded sleeve 3, it can now no longer be moved, as explained herein below, and can no longer be pulled out. This ensures that the injection device in accordance with the present invention can be used for a single dispensing operation only.

Figure 2A:
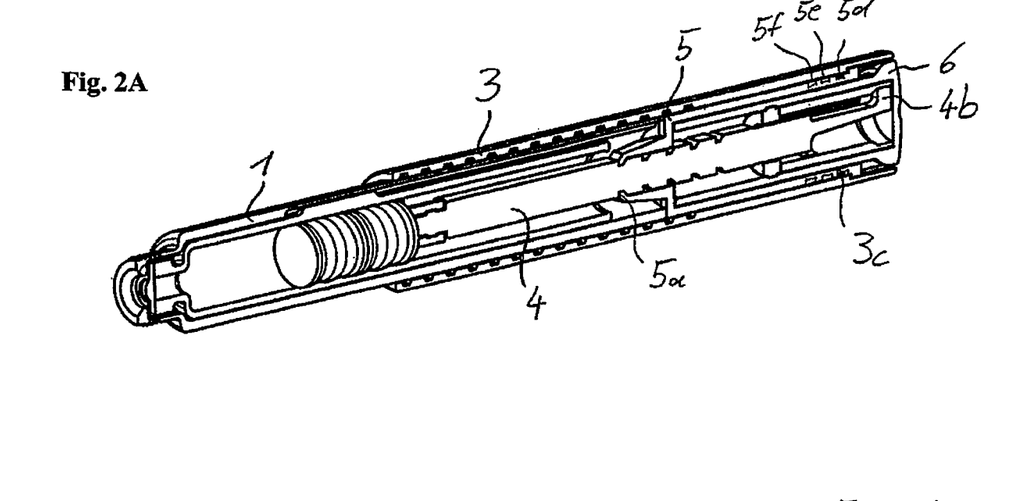
FIGS. 2A and 2B provide a view in cross-section of an injection device before and after extracting the dose setting knob.
Figure 2B:
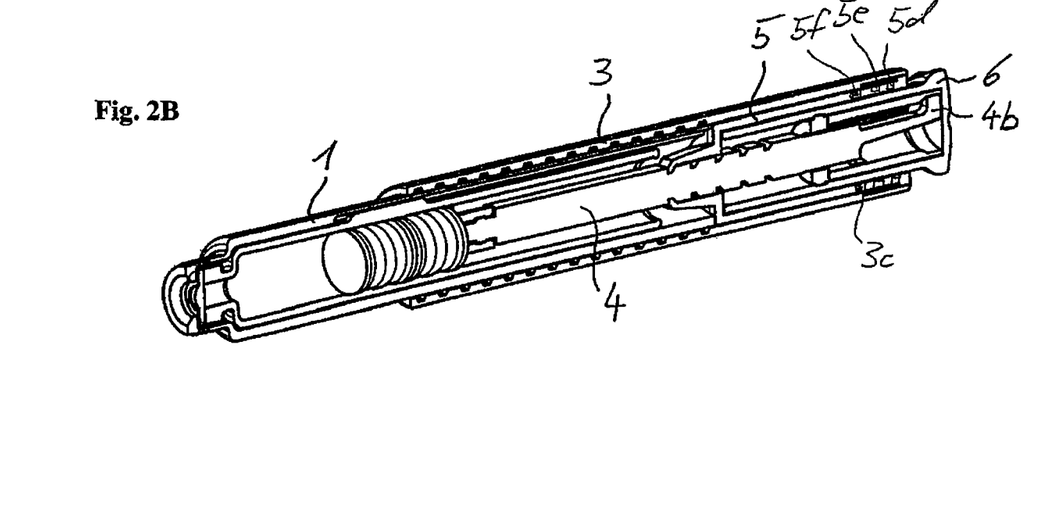

FIG. 2A is a perspective diagram in cross-section showing the dose setting knob 6 pushed in as illustrated in the initial position, which can be pushed out of the injection device by turning in or pushing in the ampoule holder 1 by the guide sleeve 5 and thus released it for a user. (See also FIG. 2B.)

Figures 3A, 3B:
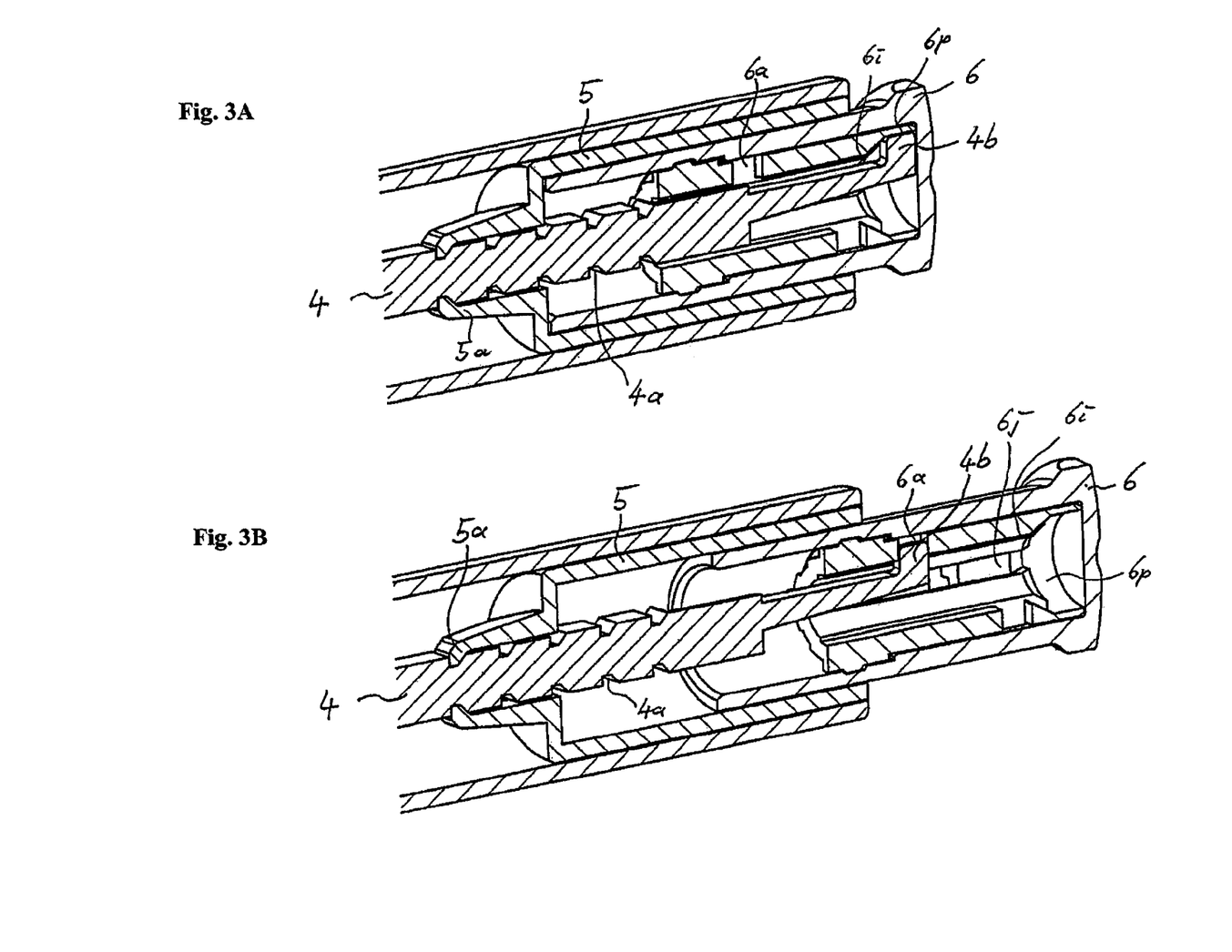
FIGS. 3A and 3B illustrate a one embodiment of a dose setting and dispensing mechanism in cross-section.

FIG. 3A is a perspective cross-section illustrating an embodiment of a setting and dispensing mechanism in accordance with the present invention, in which the dose setting knob 6 in the initial position is freely rotatable to select a dose and the snapper biased radially outwardly or the catch element 4b of the threaded rack 4 is able to revolve freely round the groove 6p, revolving around the proximal inner face of the dose setting knob 6 so that the dose setting knob 6 can also be retained. If a dose is set by a marking applied to the external circumferential face of the dose setting knob 6, the dose setting knob 6 can be pulled out of the injection device, as illustrated in FIG. 3B, until the catch element 4b, biased radially outwardly and guided by a groove 6i in the internal face of the dose setting knob 6, latches into one of several catch orifices 6a or 6b (with guide grooves 6i or 6j; see FIG. 5B) disposed in the interior of the dose setting knob 6. The set dose can be dispensed by pushing in the dose setting knob 6, which drives the threaded rack 4 with it in the distal direction and pushes it relative to the guide sleeve 5 due to the positive connection (formed by elements 6a, 4b). When the catch element 4b locates or lodges in the groove 6i of the dose setting knob 6, as illustrated in FIG. 3B, the dose setting knob is no longer freely rotatable but can be moved axially in the groove 6i until it latches in the catch orifice 6a. Having been pushed into the pen, the dose setting knob 6 can no longer be moved due to this connection (elements 4b, 6a), and due to the catch connection (elements 4a, 5a). The catch connection (elements 3c, 5f) between the threaded sleeve 3 and guide sleeve 5 is stronger than the catch connection (elements 4a, 5a) between the guide sleeve 5 and toothed rack 4, so that a pressure applied to the dose setting knob 6 will cause the toothed rack 4 to move axially forwards relative to the guide sleeve 5.

Figures 4A, 4B:
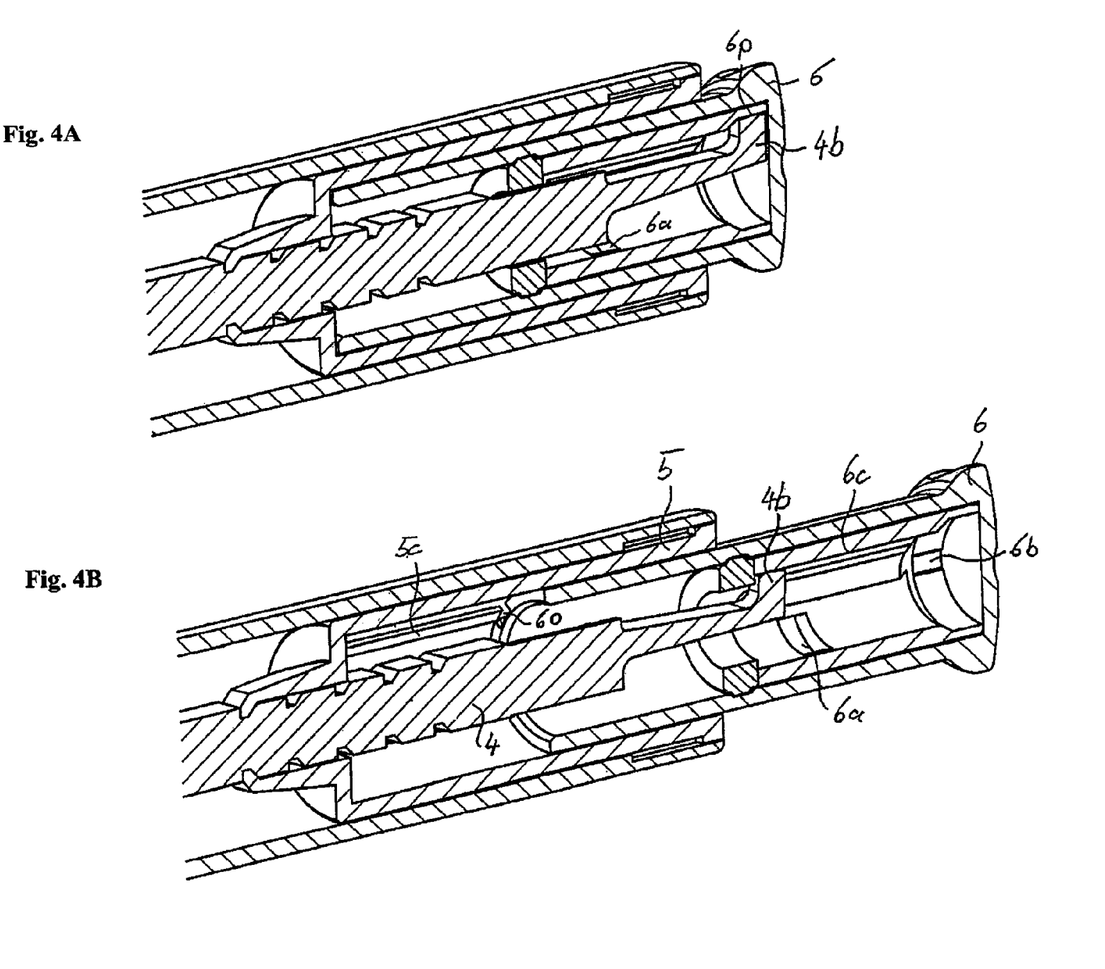
FIGS. 4A and 4B illustrate another embodiment of a dose setting and dispensing mechanism in cross-section.

FIG. 4A, in conjunction with FIG. 4B, illustrates another embodiment of a setting and dispensing mechanism in accordance with the present invention, wherein, in the position illustrated in FIG. 4A, the dose setting knob 6, releasably retained by the catch element 4b locating in the groove 6p, can no longer be radially rotated due to one or more guide bars 5c (see FIG. 4B) on the internal face of the guide sleeve 5 locating in co-operating grooves or indentations 6o in the external face of the dose setting knob 6.

When the dose setting knob 6 is pulled out of the injection device, as illustrated in FIG. 4B, the anti-rotation lock of the dose setting knob 6 is released by pushing the grooves 6o away from the guide bars, the catch element 4b runs through the empty groove 6c of the dose setting knob 6 into the setting groove 6q extending circumferentially round the internal face of the dose setting knob 6 and the dose setting knob 6 can be freely rotated to select the dose using the external face of the dose setting knob. The dose is set by catch points, recesses or orifices 6a, 6b, 6m, 6n on the internal face of the dose setting knob 6 disposed axially offset from one another in the circumferential direction with co-operating guide grooves 6i to 6l (see FIG. 5B) of differing length. When the dose setting knob 6 is pushed in, the catch element 4b moves along the guide groove 6i, 6j, 6k or 6l fixed by the rotary position of the dose setting knob 6 until it latches on the co-operating catch point 6a, 6b, 6m or 6n. When the dose setting knob 6 is pushed farther in, it drives the toothed rack 4 coupled via the catch connection of the catch element 4b with it. When the dose setting knob 6 is fully pushed in, the dose setting knob 6 can no longer be moved due to the anti-rotation lock (elements 5c, 6o) and the coupling with the toothed rack 4 which can no longer be pulled out in the proximal direction, so that the injection device is locked.

Figure 5A:
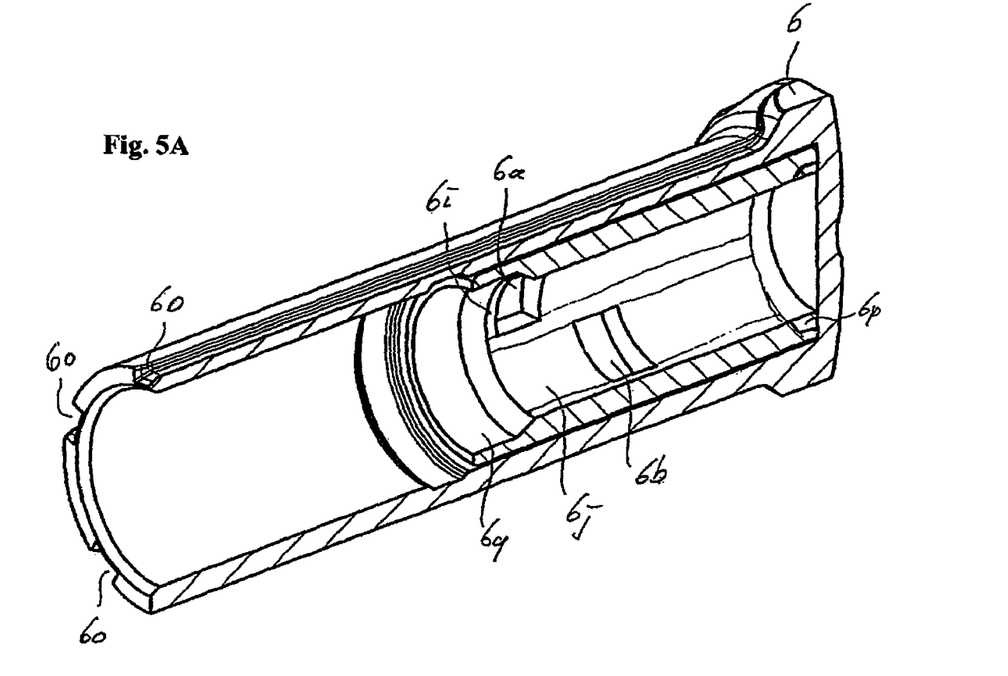
FIG. 5A is a view in cross-section showing a dose setting knob in accordance with the present invention.

FIG. 5A is a perspective view in section illustrating an embodiment of a dose setting knob 6 which may be used with both of the variants described above, with various catch orifices 6a, 6b on the internal face offset from one another in the circumferential direction and axial direction, thereby affording a latching option for the catch element 4b in one of the catch orifices 6a, 6b in each different axial direction depending on a rotary position of the dose setting knob 6. The toothed rack 4 is therefore pulled out only to the degree defined by the rotary position and the orifices 6a, 6b, 6m, 6n of the knob 6, even when the knob 6 is fully pulled out, as described in connection with the embodiment illustrated in FIG. 3. By contrast, turning to the embodiment described in connection with FIG. 4, the toothed rack is pushed in only to the degree defined by the rotary position and the orifices 6a, 6b, 6m, 6n of the knob 6.

Figure 5B:
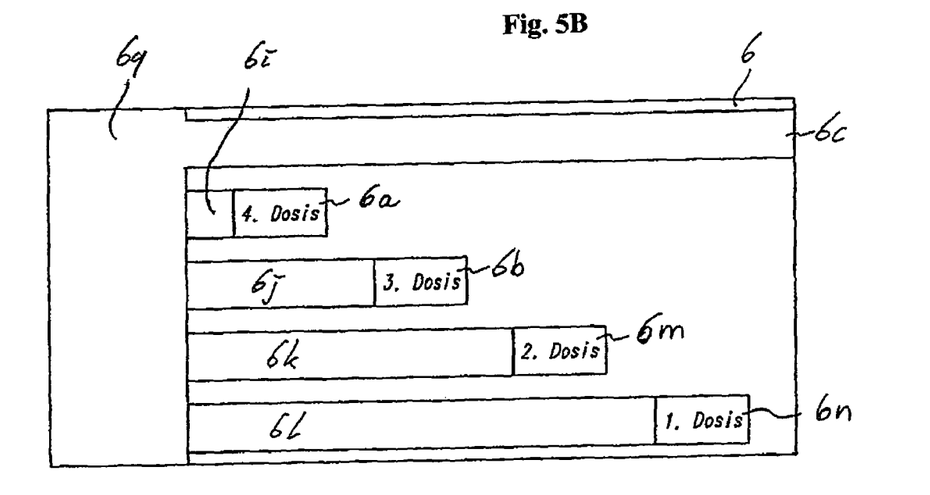
FIG. 5B is a diagram showing the internal face of the dose setting knob illustrated in FIG. 5A, but rolled out flat.

FIG. 5B is a diagram of the internal profile of the dose setting knob 6 rolled out flat, wherein, depending on the rotary position of the dose setting knob 6, different pushing paths of the toothed rack 4 for pushing the catch element 4b in can be predefined due to the grooves 6i to 6l of differing lengths, thereby enabling different doses to be dispensed. In FIG. 5B, "1st dose" represents the smallest and "4th dose" the biggest dose which can be predefined.

Figure 6A:
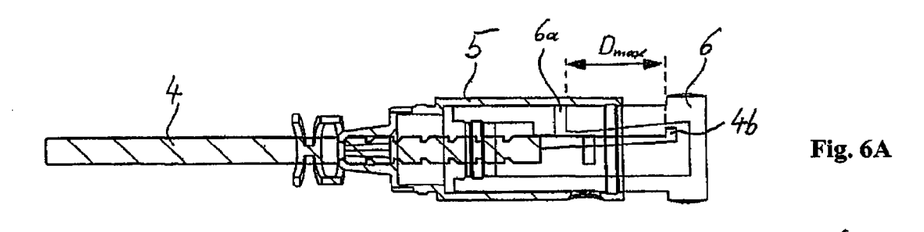
FIGS. 6A to 6C illustrate how the dispensing mechanism in accordance with the present invention co-operates with an embodiment of a toothed rack.

FIG. 6A illustrates how the setting and dose setting mechanism co-operates with the toothed rack 4 based on the embodiment illustrated in FIG. 3. As shown in FIG. 6A, the maximum stroke or dispensing movement effected by the illustrated mechanism is denoted as the distance between the catch element 4b of the toothed rack 4 and the catch orifice 6a of the dose setting knob 6 denoted by $D_{max}$.

Figure 6B:
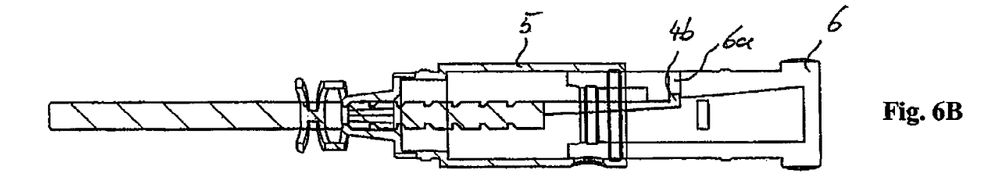
Figures 6C, 6D:
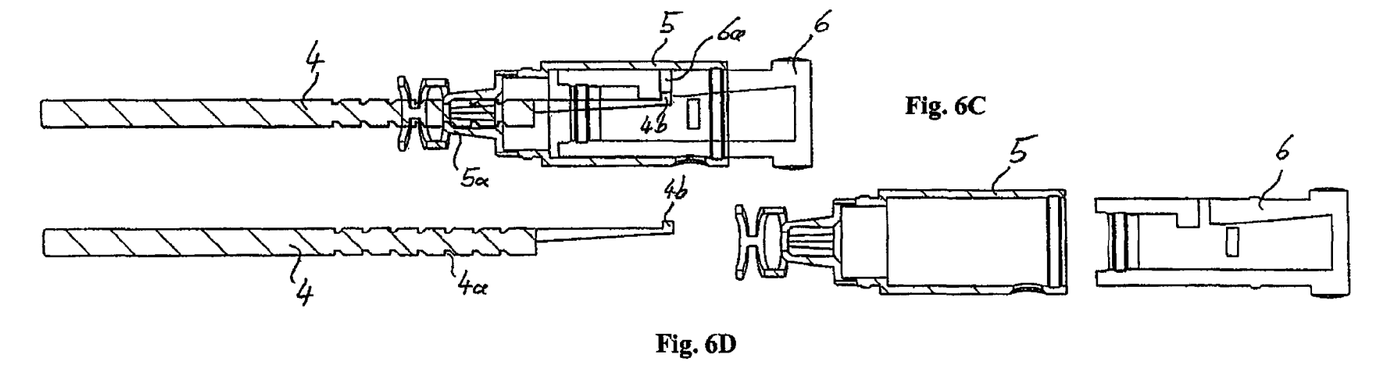
FIG. 6D is an exploded diagram of the toothed rack and dispensing mechanism.

When the dose setting knob 6 is pulled out, as illustrated in FIG. 6B, the catch element 4b latches in the catch orifice 6a and once latched in the extracted position, the dose setting knob 6 can no longer be rotated and can be pushed in so as to dispense the dose, as illustrated in FIG. 6C. In the pushed-in position, the catch lugs 5a of the guide sleeve 5 prevent the toothed rack 4 and hence the dose setting knob 6 coupled with the toothed rack 4 from being pulled out again, so that the dose setting knob 6 is locked in the position illustrated in FIG. 6C and the injection device can no longer be operated.

Instead of a catch or catch orifice such as are described with reference to FIGS. 3 to 6, one or more stops, complementary stops, steps, projecting elements, webs or cams could be provided on the dose setting knob 6. Also, the grooves 6i to 6l may be provided in the form of blind grooves or blind runs without adjoining openings.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising:
   an accommodating device for accommodating a substance to be delivered, the accommodating device insertable into and displaceable relative to the injection device;
   an adjusting element for adjusting a dose to be administered from the injection device, wherein the adjusting element has an initial position in which an external face of the adjusting element is at least partially in an interior of the injection device such that a user is substantially prevented from accessing the external face of the adjusting element to adjust the dose; and
   a coupling element for coupling the accommodating device to the adjusting element so that, when the accommodating device is inserted into the injection device, the coupling element moves the adjusting element from the initial position in a direction opposite a dispensing direction, and when the accommodating device is arranged in the injection device such that the substance can be delivered from the accommodating device, the adjustment element moves to a dose setting position in which the external face of the adjusting element is at least partially out of the interior of the injection device such that the user can access the external face of the adjusting element to adjust the dose to be administered and can push the adjusting element in the dispensing direction to deliver the dose.

2. The injection device according to claim 1, wherein the accommodating device accommodates an ampoule comprising two chambers each containing a substance to be mixed with the other.

3. The injection device according to claim 2, wherein the adjusting element is moved out of the injection device in conjunction with the mixing of the substances.

4. A method for preparing an injection device comprising a dual chamber ampoule, each chamber containing a substance to be mixed with the other substance, an accommodating device for receiving the ampoule, the accommodating device displaceable relative to the injection device, an adjusting element comprising a dose setting position in which an external face of the adjusting element is accessible for adjusting a dose of the mixed substances to be administered from the injection device and an initial position in which the external face of the adjusting element is at least partially in an interior of the injection device and prevents a user from accessing the external face to adjust the dose, and a coupling element for coupling the accommodating device to the adjusting element so that the adjusting element is pushed from the initial position to the dose setting position at least partially out of the injection device when the accommodating device is inserted into the injection device, the method comprising the steps of:
   providing the adjusting element in the injection device in the initial position,
   placing the ampoule into the accommodating device, thereby moving the adjusting element from the initial position at least partially out of the interior of the injection device in a direction opposite a dispensing direction to the dose setting position and only in conjunction with the mixing of the substances;
   using the displaced external face of the adjusting element in the dose setting position to adjust a dose to be administered; and
   administering the adjusted dose by pushing the adjusting element in the dispensing direction.

5. An injection device comprising:
   a holder device for a substance to be administered which can be displaced relative to the injection device or a part thereof,
   a setting element for setting a dose to be administered from the injection device, wherein the setting element has an initial position in which an external face of the setting element is arranged substantially in an interior of the injection device and not accessible to set a dose, a dose setting position in which the external face of the setting element is extended at least partially out of the interior of the injection device in a direction opposite a dispensing direction to allow a dose to be set using the external face, and a dose loading position in which the setting element is extended beyond the dose setting position, wherein, upon being moved from the dose setting position to the dose loading position, the injection device is loaded with the set dose and the setting element may be pushed into the injection device in the dispensing direction to deliver the dose, and
   a coupling element for coupling the holder device with the setting element so that the setting element, in the initial position, is pushed at least partially out of the interior of the injection device in the direction opposite the dispensing direction to the dose setting position during a movement introducing the holder device to the injection device.

6. The injection device as claimed in claim 5, wherein the setting element comprises a rotating knob.

7. The injection device as claimed in claim 6, wherein the knob is mounted so that it is locked to prevent it from rotating when the knob has been pushed into the initial position from the loading position or out of the injection device in the dose loading position.

8. The injection device as claimed in claim 5, wherein the setting element is coupled with the injection device so that the setting element can no longer be pushed out to the dose setting position after having been pushed into the injection device from the dose loading position.

9. The injection device as claimed in claim 5, further comprising a plunger rod or toothed rack which can be coupled with the setting element by a positive connection during or after pushing the setting element in from the dose loading position to the initial position or out from the dose setting position to the dose loading position.

10. The injection device as claimed in claim 5, wherein at least one marking is on the setting element to display the dose.

11. The injection device as claimed in claim 5, further comprising a two-chamber ampoule disposed in the holder device.

12. The injection device as claimed in claim 5, wherein the setting element is movable from the initial position to the dose setting position, and from the dose setting position to the dose loading position and back to the initial position axially along a longitudinal axis of the injection device.

13. The injection device as claimed in claim 5, wherein the setting element is not operable when in the initial position.

14. An injection device comprising:
an ampoule holder moved into the injection device;
a setting element for setting a dose to be dispensed from the injection device, which comprises an external face that can be moved in and out of an interior of the injection device, wherein when the setting element is pushed in a dispensing direction relative to the injection device, the setting element external face is non-rotatable such that a dose setting operation is prevented, and when the setting element is pushed out in a direction opposite to the dispensing direction relative to the injection device, the setting element is in a dose setting position and the external face is rotatable to allow the dose setting operation, wherein to administer the dose, the setting element is pushed in the dispensing direction; and
a coupling element for coupling the holder with the setting element so that the setting element is at least partially moved out of the interior of the injection device in a direction opposite the dispensing direction to the dose setting position during a movement of the holder device into the injection device.

15. The injection device as claimed in claim 14, wherein the setting element is a rotating knob.

16. The injection device as claimed in claim 15, wherein the setting element is mounted so that it is lockable to prevent it from rotating when moved in or out of the injection device.

17. The injection device of claim 14, further comprising a toothed rack with an end for engaging with a stopper of an ampoule within the ampoule holder to dispense the dose and a catch element at an end opposite the end for engaging with the stopper, wherein the catch element is configured to latch in a catch orifice arranged in an internal face of the setting element so as to prevent the setting element from rotating.

18. The injection device of claim 17, wherein upon latching and upon moving the setting element in relative to the injection device, the toothed rack is carried by the setting element to dispense the dose.

19. The injection device of claim 18, wherein upon the dispensing the dose, the latching engagement is retained and prevents the setting element from being pulled out relative to the injection device such that the injection device is configured for a single use.

20. The injection device as claimed in claim 14, wherein the setting element is configured so that it is locked to prevent it from rotating when the setting element has been extracted further from the injection device from the dose setting position to a loading position.

21. An injection device comprising:
a housing;
an ampoule holder for holding an ampoule containing a substance to be administered, the holder movable relative to the housing;
a setting element for setting a dose to be administered from the injection device, wherein the setting element has an initial position in which the setting element extends from a proximal end of the housing and is locked from rotating relative to the injection device, and a dosing position in which the setting element is distanced farther from the proximal end of the housing than when in the initial position and is rotatable to select a dose, wherein to administer the dose, the setting element is pushed in a distal direction; and
a coupling element for coupling the ampoule holder with the setting element so that upon coupling, the setting element is pushed at least partially out of the injection device in the proximal direction to the initial position.

22. The injection device as claimed in claim 21, wherein the coupling element comprises at least one guide bar on an internal face and cooperates with one or more cooperating grooves of an external face of the setting element to lock the setting element against rotation in the initial position.

23. The injection device as claimed in claim 22, further comprising a toothed rack comprising a catch projecting in the setting element, and wherein the setting element further comprises a plurality of catch points each corresponding to a dosage, the catch points arranged on an internal face of the setting element axially offset from one another in a circumferential direction, wherein each of the catch points comprises a guide groove, wherein when the setting element is pushed towards the ampoule, one of the guide grooves moves along the catch until the catch latches with the corresponding catch point, and upon latching, the toothed rack is driven by the setting element to deliver the dose associated with to the latched catch point.

24. The injection device as claimed in claim 23, wherein upon delivering the dose, the setting element is locked against rotation and extraction at least due to the latching engagement such that the injection device is configured for a single use.

* * * * *